United States Patent [19]

Bastian

[11] 4,081,543
[45] Mar. 28, 1978

[54] 5-SUBSTITUTED-1,2,3,4-TETRAHYDROBEN-ZO[g]ISOQUINOLINES

[75] Inventor: Jean-Michel Bastian, Therwil, Switzerland

[73] Assignee: Sandoz Ltd., Basel, Switzerland

[21] Appl. No.: 693,704

[22] Filed: Jun. 7, 1976

[30] Foreign Application Priority Data

| Jun. 13, 1975 | Switzerland | 7688/75 |
| Jun. 13, 1975 | Switzerland | 7689/75 |
| Jun. 13, 1975 | Switzerland | 7691/75 |

[51] Int. Cl.² .................. C01D 221/08; A01K 31/47
[52] U.S. Cl. .............................. 424/258; 260/283 SY; 260/287 CF; 260/288 CF; 260/294.9; 260/297 Z
[58] Field of Search ................ 260/288 CC, 287 CF; 424/258

[56] References Cited

PUBLICATIONS

Etienne et al; Chem. Abs. vol. 70:68097n (1969).

Primary Examiner—Donald G. Daus
Assistant Examiner—Mary Vaughn
Attorney, Agent, or Firm—Gerald D. Sharkin; Robert S. Honor

[57] ABSTRACT

This invention provides new compounds of formula I,

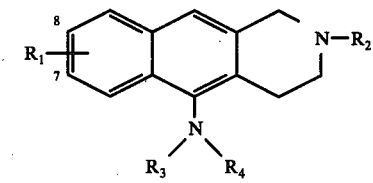

wherein
$R_1$ is hydrogen, halogen of an atomic number from 9 to 35, or alkyl or alkoxy of 1 to 4 carbon atoms,
$R_2$ is hydrogen, alkyl of 1 to 4 carbon atoms, alkenyl or alkynyl of 3 to 6 carbon atoms, in which the multiple bond is located in a position other than the $\alpha,\beta$ position, hydroxyalkyl of 2 to 5 carbon atoms in which the hydroxy group is separated from the nitrogen atom of the tricyclic ring system by at least 2 carbon atoms, alkanoylalkyl of 3 to 5 carbon atoms, or phenylalkyl of 7 to 10 carbon atoms in which the phenyl ring is unsubstituted or mono-substituted by halogen of atomic number 9 to 35, or alkyl or alkoxy of 1 to 4 carbon atoms, and
either
$R_3$ is hydrogen, alkyl of 1 to 4 carbon atoms, or phenylalkyl of 7 to 10 carbon atoms in which the phenyl ring is unsubstituted or mono-substituted by halogen of atomic number from 9 to 35, or alkyl or alkoxy of 1 to 4 carbon atoms, and
$R_4$ is hydrogen,
or
$R_3$ and $R_4$ together with the nitrogen atom to which they are bound form a 1-pyrrolyl ring,
useful as anti-aggressive and C.N.S. depressants.

27 Claims, No Drawings

5-SUBSTITUTED-1,2,3,4-TETRAHYDROBENZO[g]ISOQUINOLINES

The present invention relates to 1,2,3,4-tetrahydrobenzoisoquinolines.

The present invention provides compounds of formula I,

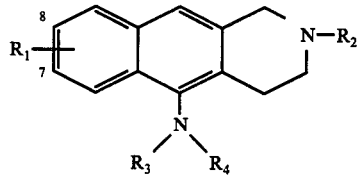

wherein
- $R_1$ is hydrogen, halogen of an atomic number from 9 to 35, or alkyl or alkoxy of 1 to 4 carbon atoms,
- $R_2$ is hydrogen, alkyl of 1 to 4 carbon atoms, alkenyl or alkynyl of 3 to 6 carbon atoms, in which the multiple bond is located in a position other than the $\alpha,\beta$ position, hydroxyalkyl of 2 to 5 carbon atoms in which the hydroxy group is separated from the nitrogen atom of the tricyclic ring system by at least 2 carbon atoms, alkanoylalkyl of 3 to 5 carbon atoms, or phenylalkyl of 7 to 10 carbon atoms in which the phenyl ring is unsubstituted or mono-substituted by halogen of atomic number 9 to 35, or alkyl or alkoxy of 1 to 4 carbon atoms, and either
- $R_3$ is hydrogen, alkyl of 1 to 4 carbon atoms, or phenylalkyl of 7 to 10 carbon atoms in which the phenyl ring is unsubstituted or mono-substituted by halogen of atomic number from 9 to 35, or alkyl or alkoxy of 1 to 4 carbon atoms, and
- $R_4$ is hydrogen, or
- $R_3$ and $R_4$ together with the nitrogen atom to which they are bound form a 1-pyrrolyl ring.

The alkyl and alkoxy moieties (except when $R_2$ is alkyl) preferably have 1 or 2 carbon atoms, especially 1 carbon atom.

$R_1$ is preferably hydrogen. Otherwise $R_1$ is preferably in the 7 or 8 position.

$R_2$ is preferably hydrogen, or alkyl. When $R_2$ is alkyl, it preferably has 1 to 3 carbon atoms, and is especially methyl or isopropyl. When $R_2$ is alkenyl or alkynyl, it preferably has 3 or 4 carbon atoms. When $R_2$ is hydroxyalkyl, it preferably has 2 or 3 carbon atoms. When $R_2$ is alkanoylalkyl it preferably contains an acetyl moiety, and preferably signifies acetonyl. When $R_2$ is phenylalkyl, this is preferably benzyl. When the phenyl ring is substituted this is preferably substituted by halogen, especially chlorine.

$R_3$ is preferably hydrogen or methyl. A preferred alternative is when $R_3$, $R_4$ and the nitrogen atom to which they are bound form a 1-pyrrolyl ring. $R_3$ when phenylalkyl is preferably an optionally substituted benzyl or phenylethyl group.

The present invention further provides a process for the production of a compound of formula I which comprises a. for the production of a compound of formula Ia,

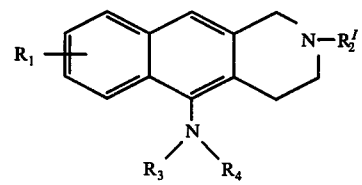

wherein
- $R_1$, $R_3$ and $R_4$ are as defined above, and
- $R_2^I$ is as defined for $R_2$ above with the proviso that $R_2^I$ is other than hydrogen, alkylating a compound of formula Ib,

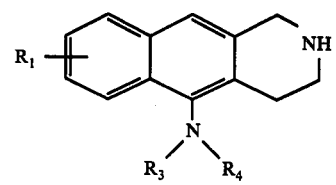

wherein
- $R_1$, $R_3$ and $R_4$ are as defined above, or b. for the production of a compound of formula Ic,

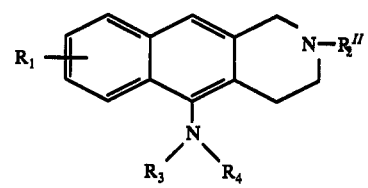

wherein
- $R_1$, $R_3$ and $R_4$ are as defined above, and
- $R_2^{II}$ is a primary alkyl group of 1 to 4 carbon atoms, or a primary unsubstituted or mono-substituted phenylalkyl as defined above for $R_2$, reducing a compound of formula II,

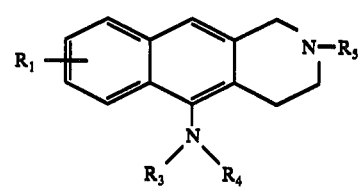

wherein
- $R_1$, $R_3$ and $R_4$ are as defined above, and
- $R_5$ is (i) alkanoyl of 2 to 4 carbon atoms, (ii) benzoyl or phenylalkanoyl of 8 to 10 carbon atoms in which benzoyl or phenylalkanoyl the phenyl ring is unsubstituted or mono-substituted by halogen or alkyl or alkoxy of 1 to 4 carbon atoms, or (iii) lower alkoxycarbonyl, or aryloxycarbonyl, or c. for the production of a compound of formula Ib, as defined above, splitting off a radical $R_5^I$ from a compound of formula III,

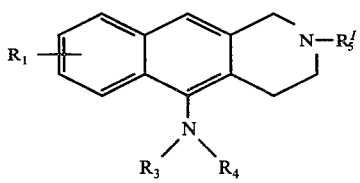

wherein
R$_1$, R$_3$ and R$_4$ are as defined above, and
R$_5{}^I$ is a group capable of being split off by solvolysis.

The introduction of the R$_2{}^I$ group as defined above according to process a) is a mono-alkylation in the 2 position of the tetrahydrobenzo[g] isoindoline residue and may be effected in known manner for such alkylations of analogous ring systems bearing in mind the other groups present. For example the compound of formula Ib may be reacted with a compound of formula IV,

R$_2{}^I$-X   IV wherein
R$_2{}^I$ is as defined above, and
X is chlorine, bromine or iodine.

An inert organic solvent may be used. Preferably there is present a medium-strong basic condensation agent, or an excess of the compound of formula Ib. As condensation agents are preferably used medium-strong organic bases such as triethylamine or pyridine or alternatively inorganic bases such as alkali metal carbonates. However, when R$_3$ is hydrogen and when a simultaneous alkylation of the 5-amino group is to be avoided then conveniently a mildly basic condensation agent is used and/or preferably approximately equivalent amounts of alkylating agent and compound of formula Ib are used. A compound of formula Ia, wherein R$_2$ is alkanoylalkyl as defined above, wherein the carbonyl group is separated by at least two carbon atoms from the nitrogen atom of the tricyclic residue, may be produced in conventional manner by using an appropriate α,β-unsaturated ketone as an alkylating agent.

The reduction according to process variant (b) may be effected in conventional manner for such reductions, e.g. using a complex metal hydride in an inert organic solvent. Suitable hydrides include complex aluminium hydrides such as lithium aluminium hydride.

Process (c) may be effected in conventional manner for the splitting off of an amino protecting group from a heterocyclic amine using solvolytic, especially hydrolytic, conditions, for example as for the splitting of a urethane or amide. Suitable protecting groups R$_5{}^I$ include for example acyl groups, preferably alkoxycarbonyl or aryloxycarbonyl groups, or alkanoyl or aroyl groups, for example those such groups defined above with respect to R$_5$. The reaction may, depending on the type of group R$_5{}^I$ used, be preferably effected in an acid medium, for example in the presence of a strong mineral acid, or in an alkaline medium, for example in the presence of a suitable inorganic base.

The starting materials may be produced as follows:
a') compounds of formula II, wherein R$_3$ is other than hydrogen may be produced in conventional manner by substituting the amino group in a compound of formula IIa,

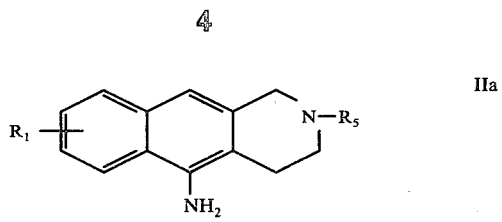

wherein R$_1$ and R$_5$ are as defined above.

For example the appropriate alkyl- or phenylalkylhalide may be used in the presence of potassium tert.-butoxide, or when R$_3$ is methyl, alternatively dimethylsulphate/pyridine may be used.

Compounds of formula II, wherein R$_3$ and R$_4$ together with the nitrogen atom to which they are bound form a 1-pyrrolyl ring may be produced by reacting a compound of formula IIa with 2,5-dimethoxytetrahydrofuran and splitting off methanol from the resulting reaction product.

b') Compounds of formula IIa may be produced from the corresponding 3-benzyl-4-piperidone derivatives of formula V,

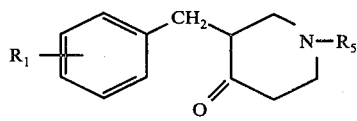

wherein R$_1$ and R$_5$ are as defined above, by (i) introducing hydrogen cyanide using conventional processes for cyanohydrin production, preferably by reaction with acetone cyanohydrin, (ii) splitting off water from the resulting 3-benzyl-4-hydroxy-4-piperidine nitrile, for example using thionyl chloride/pyridine, (iii) cyclizing the resulting 5-benzyl-4-cyano-1,2,3,6-tetrahydropyridine derivative of formula VI,

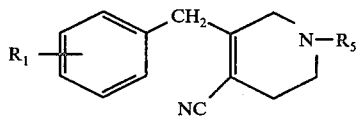

wherein R$_1$ and R$_5$ are as defined above, if desired with any corresponding 3-benzyl-4-cyano-1,2,3,6-tetrahydropyridine derivative present as a by-product, for example in the presence of 90% sulphuric acid.

Insofar as the production of any starting material is not particularly described these compounds are known, or may be produced and purified in accordance with known processes, or in a manner analogous to processes described herein, e.g. in the Examples, or to known processes.

Free base forms of compounds of formula I may be converted into acid addition salt forms in conventional manner and vice versa. Suitable acids for salt formation include hydrochloric acid or fumaric acid.

In the following Examples all temperatures are in degrees Centigrade and are uncorrected.

In the Table the following abbreviations are used:
Z = decomposition
HCl = hydrochloride salt
HBr = hydrobromide salt
Rf refers to Rf values obtained on silica gel using as eluant benzene/ethanol/(conc. aq.) ammonia 84:15:1.

EXAMPLE 1

5-Amino-2-isopropyl-1,2,3,4-tetrahydrobenzo[g]isoquinoline [process a)]

A solution of 5.2 g of isopropyl bromide in 10 ml of ethanol is added dropwise at room temperature to a mixture of 8.0 g of 5-amino-1,2,3,4-tetrahydrobenzo[g]isoquinoline [see Example 4] and 4.5 g of anhydrous sodium carbonate in 30 ml of ethanol. The reaction mixture is then boiled for 6 hours. The solvent is removed by evaporation, and the residue is treated with water. The resulting mixture is extracted with methylene chloride. The organic phase is washed with water, dried over potassium carbonate and evaporated. The title compound is obtained as a residue which is recrystallized from hexane/isopropanol (M.Pt. 112° – 113°).

EXAMPLE 2

2-Allyl-5-amino-1,2,3,4-tetrahydrobenzo[g]isoquinoline [process a)]

A mixture of 7.9 g of 5-amino-1,2,3,4-tetrahydrobenzo[g]isoquinoline, 5.3 g of allyl bromide, 2.6 g of triethylamine in 50 ml of anhydrous chloroform is heated to the boil for 4.5 hours while stirring. 100 ml of water are added to the resulting solution after cooling to room temperature, the solution is made alkaline with 40% caustic soda solution, and the organic phase is separated off. The organic solution is washed neutral with water, dried over sodium sulphate and concentrated by evaporation. The residue is recrystallized twice from methanol. M.Pt. of the title compound: 74° – 76°.

In analogous manner to Example 1 or 2, the following compounds of formula Ia may be obtained by alkylating the corresponding compounds of formula Ib with the appropriate compound of formula IV:

| Ex. No. | $R_1$ | $R_2^I$ | $R_3$ | $R_4$ | Physical constants | Produced analogous to Example |
|---|---|---|---|---|---|---|
| 2A | H | ⟨phenyl⟩—CH$_2$— | H | H | Di-HCl:mp: 248–249° (Z) | 2 |
| 2B | H | CH$_3$—CH=CH—CH$_2$— | H | H | HCl:mp: 220° (Z) | 2 |
| 2C | H | CH$_3$—CO—CH$_2$— | H | H | Rf: 0.35 | 2 |
| 2D | H | ⟨2-Cl-phenyl⟩—CH$_2$—CH$_2$— | H | H | Di-HCl:mp: Z from 245° | 2 |
| 2E | H | CH$_3$— | H | H | mp: 97–99° | 1 |
| 2F | 7-CH$_3$ | CH$_3$— | H | H | Di-HCl:mp: 237–238° (Z) | 1 |
| 2G | H | CH$_3$— | —CH=CH—CH=CH— | | HCl:mp: Z from 220° | 1 |

EXAMPLE 3

5-Amino-2-methyl-1,2,3,4-tetrahydrobenzo[g]isoquinoline [process b)]

A solution of 50.0 g of 5-amino-1,2,3,4-tetrahydrobenzo[g]isoquinolin-2-ylcarboxylic acid ethyl ester (see Example 4a–c for production) in 1.2 litres of anhydrous tetrahydrofuran is added dropwise at temperatures of between 15° – 30° to a suspension of 23.0 g of lithium aluminium hydride in 500 ml of anhydrous tetrahydrofuran while cooling. The reaction mixture is stirred for 5 hours at the boiling temperature, is cooled to 0° and is decomposed by the dropwise addition of 90 ml of a saturated sodium sulphate solution at 0° – 5°. The precipitated inorganic product is filtered off, is washed with tetrahydrofuran and concentrated by evaporation. The title compound crystallizes from the evaporation residue with the addition of ethanol and is again recrystallized from ethanol. M.Pt.: 97° – 99°.

In a manner analogous to that described in Example 3, the following compounds of formula Ic are obtained by reduction of the corresponding compounds of formula II:

| Ex. No. | $R_1$ | $R_2^{II}$ | $R_3$ | $R_4$ | M.Pt. |
|---|---|---|---|---|---|
| 3A | 7-CH$_3$ | CH$_3$— | H | H | Di-HCl: 237–238° (Z) |
| 3B | H | ⟨2-Cl-phenyl⟩—CH$_2$—CH$_2$— | H | H | Di-HCl: Z from 245° |
| 3C | H | ⟨phenyl⟩—CH$_2$— | H | H | Di-HCl: 248–249° (Z) |
| 3D | H | CH$_3$— | —CH=CH—CH=CH— | | HCl: Z from 220° |

EXAMPLE 4

5-Amino-1,2,3,4-tetrahydrobenzo[g]isoquinoline [process c)]

80 ml of 48% hydrobromic acid are added dropwise at room temperature to a solution of 9.6 g of 5-amino-1,2,3,4-tetrahydrobenzo[g]isoquinolin-2-yl-carboxylic acid ethyl ester in 80 ml of glacial acetic acid and are heated to the boil for 3.5 hours. The cooled reaction mixture is poured into ice, is adjusted to pH 12–13 by the addition of 40% caustic soda solution and is extracted with methylene chloride. The organic solution is washed neutral with water, is dried over sodium sulphate, concentrated by evaporation and the solid residue is recrystallized twice from benzene. M.Pt. of the title compound: 150° – 152°.

The starting material may be produced as follows:
a) 15.6 g of acetone cyanohydrin are added to 47.5 g of 3-benzyl-4-oxopiperidin-1-ylcarboxylic acid ethyl ester, and after the addition of a small amount of potassium carbonate moistened with methanol, the reaction mixture is stirred for 5 – 8 hours at room temperature. 20 ml of ether and 20 ml of petroleum ether are added to the pasty reaction mixture paste after 5 – 10 hours at room temperature and the solid product is filtered with suction, washed again and dried at 50°. M.Pt. of the resulting 3-benzyl-4-cyano-4-hydroxpiperidin-1-ylcarboxylic acid ethyl ester: 120° – 121° (from ether/petroleum ether).
b) 6.5 of thionyl chloride are added dropwise at 5° to a solution of 16.0 g of the product obtained in step (a) in 20 ml of anhydrous pyridine and 14 ml of anhydrous benzene. The reaction mixture is allowed to stand for 5 hours at 0° – 5° and for 12 hours at room temperature, is poured into 100 ml of icewater, and the organic phase is separated off. The organic solution is washed with water, dried over magnesium sulphate and concentrated by evaporation. The 5-benzyl-4-cyano-1,2,3,4-tetrahydropyridin-1-yl-carboxylic acid ethyl ester (IR: CN band at 2230 cm$^{-1}$) containing the resulting oil is further worked up in the crude state.
c) 70 ml of 90% sulphuric acid are added to 9.8 g of the product obtained in step (b) while stirring vigorously, so that the temperature does not exceed 5°. The mixture is allowed to stand for one hour at 5° and for 3–4 hours at room temperature with occasional shaking. The resulting uniform solution is poured into 500 g of ice and is extracted with methylene chloride. The aqueous solution is adjusted to pH 9–10 by the addition of 40% caustic soda solution and is again extracted with methylene chloride. The combined extracts are washed with water, are dried over magnesium sulphate and are concentrated by evaporation under a nitrogen atmosphere. The solid 5-amino-1,2,3,4-tetrahydrobenzo[g]isoquinolin-2-ylcarboxylic acid ethyl ester remaining as evaporation residue is recrystallized from ethyl acetate. M.Pt.: 198° (decomposition).

EXAMPLE 5

5-(1-pyrrolyl)-1,2,3,4-tetrahydrobenzo[g]isoquinoline [process c)]

A mixture of 2.0 g of 5-(1-pyrrolyl)-1,2,3,4-tetrahydrobenzo[g]isoquinolin-2-yl-carboxylic acid ethyl ester and 4.0 g of potassium hydroxide in 20 ml of n-butanol is boiled for 2 hours. After cooling to room temperature, the mixture is diluted with benzene, washed neutral with water and extracted 3 times with a 10% aqueous tartaric acid solution. The acid solution is washed with ether, made alkaline by the addition of 40% caustic soda solution and extracted with benzene. The benzene extract is washed with water and dried over magnesium sulphate. The title compound is obtained by evaporation of the benzene solvent and converted into the hydrochloride salt having a M.Pt. from 240° (decomposition).

The starting material is produced as follows:
a) A mixture of 30 g of 5-amino-1,2,3,4-tetrahydrobenzo[g]isoquinolin-2-yl-carboxylic acid ethyl ester, 14.7 g of 2,5-dimethoxytetrahydrofuran and 150 ml of ethyl acetate is boiled for 30 minutes and then cooled to room temperature. A solution of 11.1 g of potassium hydroxide in 75 ml of methanol and 75 ml of water is added and the reaction mixture is again boiled for 5 hours with stirring. The resulting reaction solution after cooling to 20° is poured into ice, adjusted to pH 2–3 with concentrated hydrochloric acid and extracted with ether. The ether extracts are washed with water and saturated brine, dried over sodium sulphate and evaporated. The evaporation residue, 5-(1-pyrrolyl)-1,2,3,4-tetrahydrobenzo[g]isoquinolin2-yl-carboxylic acid ethyl ester is crystallized twice from ether/petroleum ether. M.Pt.: 109° – 111°.

In a manner analogous to Example 4 or 5 the following compounds of formula Ib may be produced by splitting off the $R_5^I$ group from the corresponding compound of formula III.

| Ex. | Compound of formula Ib | | | | Compound of formula III | | | | |
|---|---|---|---|---|---|---|---|---|---|
| No. | $R_1$ | $R_3$ | $R_4$ | M.Pt. | $R_1$ | $R_3$ | $R_4$ | $R_5^I$ | M.Pt. |
| 5A | 7-CH$_3$ | H | H | di-HCl: 254–255° | 7-CH$_3$ | H | H | COOC$_2$H$_5$ | 154–156° (Z) |
| 5B | H | CH$_3$ | H | Di-HBr: 255–258° (Z) | H | CH$_3$ | H | COOC$_2$H$_5$ | HCl: 214–215° |

The starting material for Example 5B may be obtained as follows:
a. 3 ml of pyridine are added to a mixture of 27.0 g of 5-amino-1,2,3,4-tetrahydrobenzo[g]isoquinolin-2-ylcarboxylic acid ethyl ester in 50 ml of water. 50.4 g of dimethyl sulphate are added dropwise to this mixture within 10 minutes and the mixture is stirred for 8 hours at 55° – 60°. The resulting clear solution is diluted with 100 ml of water, and is extracted several times with chloroform. The extracts are washed neutral with water, are dried over sodium sulphate and concentrated by evaporation. The oily residue is taken up in ether, is made acid with ethereal hydrochloric acid solution and the precipitated product is filtered off and recrystallized from ethanol/ether. M.Pt. of 5-methylamino-1,2,3,4-tetrahydrobenzo[g]isoquinolin-2-ylcarboxylic acid ethyl ester hydrochloride 214° – 215°.

In analogous manner to Example 1 the following compounds of formula I may be obtained, wherein $R_4$ is hydrogen, and

| | $R_1$ | $R_2$ | $R_3$ |
|---|---|---|---|
| a) | 9-Br | $[CH_2]_4 \cdot C{\equiv}CH$ | $[CH_2]_4$—⟨phenyl⟩ |
| b) | 6-$C_2H_5O$ | $[CH_2]_5OH$ | $[CH_2]_4$—⟨phenyl⟩—$O^n$-$[C_4H_9]$ |
| c) | 7-$C_2H_5O$ | —$[CH_2]_4$—⟨phenyl⟩—$O^n[C_4H_9]$ | $[CH_2]_4$—⟨phenyl⟩-$^nC_4H_9$ |
| d) | 7-$C_2H_5O$ | 1-$[CH_2]_4$—⟨phenyl⟩-$O^n[C_4H_9]$ | —$[CH_2]_4$—⟨phenyl⟩-F |

The compounds of formula I are useful because they exhibit pharmacological activity. In particular the compounds exhibit anti-aggressive activity, e.g. for the treatment of aggression in psychopaths and imbeciles as indicated in standard tests. In one standard test the compounds inhibit isolation-induced aggressive behaviour according to the method of H.C.Y. Yen et al [J. Pharmacol. exp. Ther. 122, 85A (1958)].

The compounds are administered p.o. at a dose of from 1 to about 100 mg/kg animal body weight. The compounds exhibit significant activity on p.o. administration in the well known climbing test with mice at higher doses than those at which they are significantly effective in the anti-aggression test.

Interesting compounds are those wherein $R_1$, $R_2$ and $R_4$ are all hydrogen and those wherein $R_3$ and $R_4$ together with the nitrogen atom to which they are bound form a 1-pyrrolyl ring and $R_2$ is other than hydrogen. The Example 4 compound exhibits especially interesting activity.

For the above mentioned use the dosage will, of course, vary depending on the compound employed, mode of administration and therapy desired. However, in general, satisfactory results are obtained when administered at a daily dosage of from 0.3 mg to about 30 mg per kg animal body weight, conveniently given in divided doses 2 to 4 times a day or in sustained release form. For the larger mammal, the total daily dosage is in the range from about 20 to about 200 mg, and dosage forms suitable for oral administration comprise from about 5 mg to about 100 mg of the compounds admixed with a solid or liquid pharmaceutical carrier or diluent.

The compounds are furthermore useful as central nervous system depressants, e.g. for the psychiatric treatment of excitation, as indicated by their activity in the above-mentioned climbing test.

Interesting compounds are those wherein $R_2$ is optionally substituted phenylalkyl. The Example 3B compound exhibits notable activity.

For this use the dosage will, of course, vary depending on the compound employed, mode of administration and therapy desired. However, in general, satisfactory results are obtained when administered at a daily dosage of from 0.3 mg to about 100 mg per kg animal body weight, conveniently given in divided doses 2 to 4 times a day or in sustained release form. For the larger mammal, the total daily dosage is in the range from about 20 to about 200 mg, and dosage forms suitable for oral administration comprise from about 5 mg to about 100 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be in the form of, for example, a solution or a tablet.

In a group of compounds $R_3$ is hydrogen, alkyl or substituted or unsubstituted phenylalkyl. In a sub-group $R_2$ is hydrogen.

In another group of compounds $R_2$ is hydrogen, alkyl or unsubstituted or substituted phenylalkyl and $R_3$ and $R_4$ are both hydrogen.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

I claim:

1. A compound of formula I,

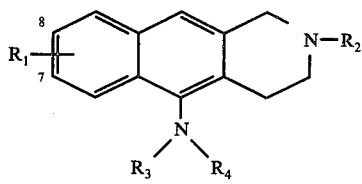

wherein
$R_1$ is hydrogen, halogen of an atomic number from 9 to 35, or alkyl or alkoxy of 1 to 4 carbon atoms,
$R_2$ is hydrogen, alkyl of 1 to 4 carbon atoms, alkenyl or alkynyl of 3 to 6 carbon atoms, in which the multiple bond is located in a position other than the α,β position, hydroxyalkyl of 2 to 5 carbon atoms in which the hydroxy group is separated from the nitrogen atom of the tricyclic ring system by at least 2 carbon atoms, alkanoylalkyl of 3 to 5 carbon atoms, or phenylalkyl of 7 to 10 carbon atoms in which the phenyl ring is unsubstituted or monosubstituted by halogen of atomic number 9 to 35, or alkyl or alkoxy of 1 to 4 carbon atoms, and
either
$R_3$ is hydrogen, alkyl of 1 to 4 carbon atoms, or phenylalkyl of 7 to 10 carbon atoms in which the phenyl ring is unsubstituted or mono-substituted by halogen of atomic number from 9 to 35, or alkyl or alkoxy of 1 to 4 carbon atoms, and
$R_4$ is hydrogen,
or
$R_3$ and $R_4$ together with the nitrogen atom to which they are bound form a 1-pyrrolyl ring,
in the form of the free base or in the form of a pharmaceutically acceptable acid addition salt thereof.

2. A compound of claim 1, wherein $R_3$ is hydrogen, alkyl or substituted or unsubstituted phenylalkyl.

3. A compound of claim 2, wherein $R_2$ is hydrogen.

4. A compound of claim 1, wherein $R_2$ is hydrogen, alkyl or unsubstituted or substituted phenylalkyl, and $R_3$ and $R_4$ are both hydrogen.

5. A pharmaceutical composition comprising an anti-aggressive or anti-excitation effective amount of a compound according to claim 1 in association with a pharmaceutical carrier or diluent.

6. A method of treating excitation or aggression in animals which comprises administering to an animal in need of such treatment a therapeutically effective amount of a compound of claim 1.

7. The method of claim 6 wherein the compound is 5-amino-1,2,3,4-tetrahydro[g]benzoisoquinoline or a pharmaceutically acceptable acid addition salt thereof.

8. The method of claim 6 wherein the compound is 5-amino-2-(o-chlorophenethyl)-1,2,3,4-tetrahydrobenzo[g]isoquinoline or a pharmaceutically acceptable addition salt thereof.

9. A compound of claim 1 where $R_1$, $R_2$ and $R_4$ are hydrogen and $R_3$ is as defined in claim 1, or a pharmaceutically acceptable acid addition salt thereof.

10. A compound of claim 1 wherein $R_1$ is as defined in claim 1, $R_2$ is other than hydrogen, and $NR_3R_4$ represents 1-pyrrolyl, or a pharmaceutically acceptable acid addition salt thereof.

11. A compound of claim 1 which is 5-amino-1,2,3,4-tetrahydrobenzo[g]isoquinoline or a pharmaceutically acceptable acid addition salt thereof.

12. A compound of claim 1 where $R_1$, $R_3$ and $R_4$ are as defined in claim 1 and $R_2$ is phenylalkyl of 7 to 10 carbon atoms in which the phenyl ring is unsubstituted or mono-substituted by halogen of atomic number 9 to 35, or alkyl or alkoxy of 1 to 4 carbon atoms, or a pharmaceutically acceptable acid addition salt thereof.

13. A compound of claim 1 which is 5-amino-2-(o-chlorophenethyl)-1,2,3,4-tetrahydro[g]benzoisoquinoline, or a pharmaceutically acceptable acid addition salt thereof.

14. A compound of claim 1 where $R_1$, $R_2$ and $R_4$ are as defined in claim 1 and $R_3$ is hydrogen, alkyl of 1 to 4 carbon atoms or phenylalkyl of 7 to 10 carbon atoms in which the phenyl ring is unsubstituted or mono-substituted by halogen of atomic number from 9 to 35, or alkyl or alkoxy of 1 to 4 carbon atoms, or a pharmaceutically acceptable acid addition salt thereof.

15. A compound of claim 1 where $R_1$ is as defined in claim 1, $R_2$ is hydrogen, alkyl of 1 to 4 carbon atoms or phenylalkyl of 7 to 10 carbon atoms in which the phenyl ring is unsubstituted or mono-substituted by halogen or atomic number 9 to 35, or alkyl or alkoxy of 1 to 4 carbon atoms, a and $R_3$ and $R_4$ are each hydrogen, or a pharmaceutically acceptable acid addition salt thereof.

16. A compound of claim 1 which is 5-amino-2-isopropyl-1,2,3,4-tetrahydrobenzo[g]isoquinoline or a pharmaceutically acceptable acid addition salt thereof.

17. A compound of claim 1 which is 2-allyl-5-amino-1,2,3,4-tetrahydrobenzo[g]isoquinoline or a pharmaceutically acceptable acid addition salt thereof.

18. A compound of claim 1 which is 5-amino-2-benzyl-1,2,3,4-tetrahydrobenzo[g]isoquinoline or a pharmaceutically acceptable acid addition salt thereof.

19. A compound of claim 1 which is 5-amino-2-(2-butenyl)-1,2,3,4-tetrahydrobenzo[g]isoquinoline or a pharmaceutically acceptable acid addition salt thereof.

20. A compound of claim 1 which is 2-acetonyl-5-amino-1,2,3,4-tetrahydrobenzo[g]isoquinoline or a pharmaceutically acceptable acid addition salt thereof.

21. A compound of claim 1 which is 5-amino-2-methyl-1,2,3,4-tetrahydrobenzo[g]isoquinoline or a pharmaceutically acceptable acid addition salt thereof.

22. A compound of claim 1 which is 5-amino-2,7,-dimethyl-1,2,3,4-tetrahydrobenzo[g]isoquinoline or a pharmaceutically acceptable acid addition salt thereof.

23. A compound of claim 1 which is 2-methyl-5-(1-pyrrolyl)-1,2,3,4-tetrahydrobenzo[g]isoquinoline or a pharmaceutically acceptable acid addition salt thereof.

24. A compound of claim 1 which is 5-(1-pyrrolyl)-1,2,3,4-tetrahydrobenzo[g]isoquinoline or a pharmaceutically acceptable acid addition salt thereof.

25. A compound of claim 1 which is 5-amino-7-methyl-1,2,3,4-tetrahydrobenzo[g]isoquinoline or a pharmaceutically acceptable acid addition salt thereof.

26. A compound of claim 1 which is 5-methylamino-1,2,3,4-tetrahydrobenzo[g]isoquinoline or a pharmaceutically acceptable acid addition salt thereof.

27. A compound of claim 14 where $R_2$ is hydrogen.

* * * * *